US00PP09405P

United States Patent [19]

Moore

[11] Patent Number: Plant 9,405

[45] Date of Patent: Dec. 19, 1995

[54] FLORIBUNDA ROSE PLANT NAMED 'MORFLASH'

[75] Inventor: Ralph S. Moore, Visalia, Calif.

[73] Assignee: Weeks Wholesale Rose Grower, Inc., Upland, Calif.

[21] Appl. No.: 342,092

[22] Filed: Nov. 18, 1994

[51] Int. Cl.[6] ..... A01H 5/00

[52] U.S. Cl. ..... Plt./22

[58] Field of Search ..... Plt./12, 22, 27, Plt./28

*Primary Examiner*—Howard J. Locker

*Attorney, Agent, or Firm*—Christie, Parker & Hale

[57] ABSTRACT

A new variety of Floribunda rose suitable for garden decoration, having flowers of two-toned scarlet and white coloration.

1 Drawing Sheet

BACKGROUND OF THE INVENTION

This invention relates to a new and distinct variety of Floribunda Rose. The varietal denomination of the new variety is 'Morflash'. The plant is bushy and upright and cultivated for outdoor garden decoration. It has as its seed parent 'Orangeade' and as its pollen parent 'Macmanly' (U.S. Plant Pat. No. 6,907).

SUMMARY OF THE INVENTION

Among the features which distinguish the new variety 'Morflash' from other presently available and known commercial rose cultivars are the following combination of charcteristics: its extreme thorniness with prickles of all sizes, its very long lasting flowers, its novel bicolor coloration of scarlet orange and white, and its abundant production of large sprays. 'Morflash' may be asexually propagated by cuttings, budding, and grafting.

Asexual reproduction of the new variety as performed in Kern County and Upland, Calif., by budding shows that the foregoing and other distinguishing characteristics come true to form and are established and transmitted through succeeding propagations.

COMPARISON WITH PARENT VARIETIES

The new rose may be distinguished from its seed parent, 'Orangeade' by the following combination of characteristics: whereas 'Morflash' produces mostly large sprays of flowers, the seed parent is less likely to produce sprays and the sprays are significantly smaller. 'Orangeade' produces moderably large flowers of single petalage, whereas the new variety produces smaller flowers with more double petalage. The flowers of 'Orangeade' are a clear orange coloration, whereas 'Morflash' has a bicolor coloration of scarlet orange and white.

The new variety may be distinguished from its pollen parent, 'Macmanly' by the following combination of characteristics: whereas the pollen parent is classified as a Miniature with small flowers and foliage, the new seedling is classified as a Floribunda with significantly larger flowers and foliage. 'Morflash' produces fully double flowers of scarlet orange and white coloration, whereas 'Macmanly' produces semi-double flowers of red and white coloration.

BRIEF DESCRIPTION OF ILLUSTRATION

The accompanying photograph illustrates the new variety and shows the flowering thereof from bud to full bloom depicted in color as nearly correct as it is possible to make in a color illustration of this character. Throughout this specification, color values are based upon the Colour Chart of The Royal Horticultural Society of London, England, except where common terms of color definition are employed.

DESCRIPTION OF THE NEW VARIETY

The following description is of rose plants of the new cultivar grown outdoors in Wasco, Calif. in the month of September. Phenotypic expression may vary with environmental, cultural and climatic conditions, as well as differences in conditions of light and soil.

FLOWER

The new variety usually bears several flowers per stem. Flowers are borne in irregular flat to rounded clusters on normal strong medium length stems (about 14 to about 20 cm.), for the class. Outdoors the plant blooms very abundantly and nearly continuously during the growing season. The flowers have a slight apple-like fragrance.

BUD

The peduncle is moderately long for the class (about 6 to about 9 cm.), and usually erect. It is moderately rought, with numerous stipitate glands and few small prickles. Peduncle color is between 144B and 138B sometimes lightly suffused with near 183B.

Before the calyx breaks, the bud is of small to medium size for the class (about 1.5 cm. in diameter at the widest point), moderately short to medium in length (about 2 to about 2.5 cm.), and pointed to ovoid in shape. The surface of the bud bears some stipitate glands usually with slender foliaceous parts extending beyond the tip of the bud equal to ¼ or more of its length. Bud color is between 144B and 138B often moderately suffused with near 183B.

The inner surface of the sepals is covered with fine wooly tomentum; sepal margins are lined with few stipitate glands and hairs.

As the petals open, the bud is moderately small to medium for the class (about 1.5 to about 2 cm. in diameter at the widest point), moderately short to medium in length (about 2.5 cm.), and somewhat pointed to ovoid in form. The color of the under surfaces of the newly opened petals is between 36A and 36D with a medium sized attachment zone at the base of near 2D. Areas hit by the sun blush to between 42B and 45D. The color of the upper surfaces of the newly opened petals is between 45A and 45C with as moderately large attachment zone at the base of near 4A. The bud does open up wall and is not prevented from opening by wet, hot or dry weather.

BLOOM

When fully open, the bloom is somewhat small to medium for the class, ranging from about 6 to about 7 cm. in diameter. Petalage is double with 31 to 37 petals and 4 to 7 petaloids arranged irregularly. When partially open, the bloom form is moderately flat to cupped and the petals are somewhat loosely cupped and undulated. When fully open, the bloom form is somewhat more cupped to flat and the petals are more loosely cupped to undulated with petal edges very slightly reflexed outward.

PETALS

The petals are of moderately heavy to somewhat crisp substance and moderately thick with upper surfaces satiny and under surfaces slightly shiny. The outer petals are nearly round to broadly obovate in shape with mucronate apices. The inner petals are usually obovate in shape with mucronate apices.

NEWLY OPENED FLOWER

The under surface of the outer, intermediate and inner petals is between 36D and 155A with a medium sized attachment zone at the base of near 2D. The upper surface of the outer, intermediate and inner petals is between 44B and 45C with a moderately large attachment zone at the base of near 4A.

The general tonality of the newly opened flower is between 44B and 45C with a reverse of between 36D and 155A.

THREE DAY OLD FLOWER

The under surface of the outer and inner petals is near 155A. The upper surface of the outer and inner petals is between 43C and 47D with a moderately large attachment zone at the base of near 155A.

The general tonality of the three day old flower is between 43C and 47D with a reverse of near 155A.

Petals on spent bloom usually drop off cleanly.

In September, in Wasco, Calif., blooms on the bush growing outdoors generally last from five or more days. Cut roses grown outdoors and kept at normal indoor living temperatures generally last from six or more days.

MALE REPRODUCTIVE ORGANS

Stamens are arranged regularly about the pistil; a few are mixed with petaloids and tucked in the receptacle. The filaments are short, most with anthers. The anthers are small and all open approximately at the same time. Anther color is near 17A when immature and near 165B at maturity. Pollen is sparse, near 12B in color.

FEMALE REPRODUCTIVE ORGANS

Pistils are very abundant (approximately 135). The styles are uneven, short, and bunched. Stigma and style color is near 4A. Ovaries are usually all enclosed in the calyx.

Hips are globular in form, and near 17B in color when ripe. The hip surface is very smooth with thick fleshy walls. Seeds are average in number (approximately 12 to 16).

FOLIAGE

The compound leaves are usually comprised of three to five and occasionally seven leaflets and are borne abundantly. The leaves are somewhat small to medium for the class (about 9 to about 11 cm. in length and about 7 to about 8 cm. in width at the widest point), moderately heavy to crisp in texture, and semi-glossy in finish. The leaflets are somewhat small to medium for the class (about 4.5 to about 5.5 cm. in length and about 2.5 cm. in width at the widest point), shaped moderately oval to ovate with acute apices and acute to round bases. Their margins are very dentate.

The upper surface of the mature leaf is between 147A and 139l A. The under surface of the mature leaf is between 148B and 189B. The upper and under surface of the young leaf is between 147B and 138B, often heavily suffused with between 187A and 183A.

The rachis is grooved with some hairs and stipitate glands on the edges of the upper side. The under side of the rachis is somewhat rough with some hairs and stipitate glands and 2 to 4 small prickles.

The stipules have short to medium straight points that usually turn out at an angle of less than 45 degrees.

The plant displays resistance to powdery mildew and rust as compared to other commercial varieties grown under comparable conditions in Wasco, Calif.

GROWTH

The plant is very vigorous and has a bushy upright medium to tall habit (about 110 to about 120 cm. in height and about 70 to about 80 cm. spread at the widest point), and is moderately full branching.

The color of the major stems is between 146C and 146D. They bear numerous almost straight prickles of many sizes; prickle color is near to between 166B and 166C.

The color of the branches is between 146B and 138B. They bear numerous prickles of many sizes; prickle color is near to between 160B and 160C.

The color of the new shoots is between 144B and 138B, often suffused with near 183A. They bear numerous prickles of many sizes which are moderately long and almost straight with a somewhat medium length to long moderately broad base; prickle color is near to between 145A and 144C, sometimes lightly suffused at the base with near 183A.

I claim:

1. A new and distinct variety of Floribunda rose substantially as described and illustrated herein.

* * * * *

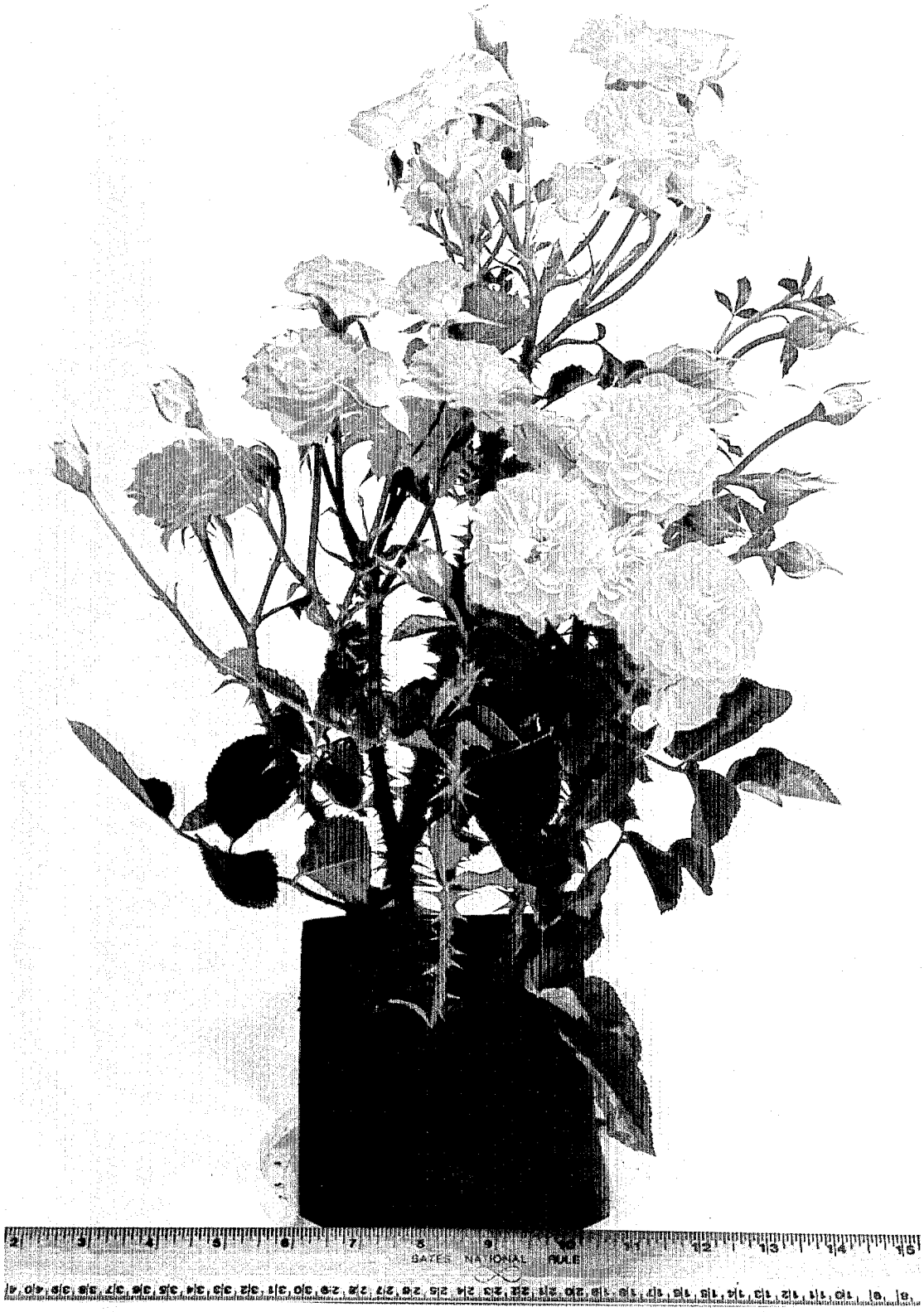
BATES NATIONAL RULE

UNITED STATES PATENT AND TRADEMARK OFFICE

CERTIFICATE OF CORRECTION

PATENT NO. : Plant 9,405

DATED : December 19, 1995

INVENTOR(S) : Ralph S. Moore

It is certified that error appears in the above-indentified patent and that said Letters Patent is hereby corrected as shown below:

Column 2, line 23, change "rought" to -- rough --.

Column 2, line 46, change "as moderately" to -- a moderately --.

Column 2, line 48, change "wall" to -- well --.

Column 4, line 20, change "1391 A" to -- 139A --.

Signed and Sealed this

Seventh Day of January, 1997

Bruce Lehman

*Attest:*

BRUCE LEHMAN

*Attesting Officer*

*Commissioner of Patents and Trademarks*